United States Patent [19]

Kleefeld et al.

[11] Patent Number: 5,166,165
[45] Date of Patent: Nov. 24, 1992

[54] FUNGICIDAL AGENTS BASED ON HETEROCYCLICALLY SUBSTITUTED SULPHONES

[75] Inventors: Gerd Kleefeld, Duesseldorf; Hans-Joachim Diehr, Wuppertal; Wilhelm Haas; Kerpen; Heinz-Wilhelm Dehne, Monheim; Wilhelm Brandes, Leichlingen, all of Fed. Rep. of Germany

[73] Assignee: Bayer Aktiengesellschaft, Leverkusen, Fed. Rep. of Germany

[21] Appl. No.: 775,632

[22] Filed: Oct. 10, 1991

[30] Foreign Application Priority Data

Oct. 20, 1990 [DE] Fed. Rep. of Germany ....... 4033412

[51] Int. Cl.$^5$ .............................................. A01N 43/82
[52] U.S. Cl. ..................... 514/364; 514/363
[58] Field of Search ......................... 514/364

[56] References Cited

U.S. PATENT DOCUMENTS 4,929,628  5/1990  McArthur et al. ................. 514/364

OTHER PUBLICATIONS

Agricultural and Biological Chemistry, vol. 40, 1976.
Chemical Abstracts, vol. 108, 1988.
Giri et al. vol. 84, (1976) 121,736N.

*Primary Examiner*—Allen J. Robinson
*Attorney, Agent, or Firm*—Sprung Horn Kramer & Woods

[57] ABSTRACT

Use of compounds of the formula (I)

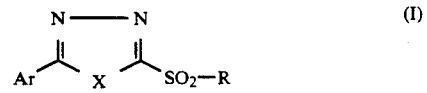

in which
Ar, R and X have the meaning indicated in the description, for combating phytopathogenic fungi in agriculture.

The compounds of the formula (I), are known and can be prepared by analogous processes, for example by oxidizing the corresponding thio compounds, for example using potassium permanganate.

4 Claims, No Drawings

FUNGICIDAL AGENTS BASED ON HETEROCYCLICALLY SUBSTITUTED SULPHONES

The invention relates to the use of heterocyclically substituted sulphones as fungicides against phytopathogenic pathogens in agriculture.

It is known that certain heterocyclically substituted sulphones such as, for example, the compound 2-[(4-methyl-3-nitrophenyl)-sulphonyl]-5-trifluoromethyl-1,3,4-thiadiazole have a fungicidal activity against phytopathogenic pathogens in agriculture (compare, for example, DE 2,533,604).

However, the activity of these previously known compounds is not entirely satisfactory in all fields of application, in particular when low dosage rates and concentrations are applied.

Furthermore, it is known that certain heterocyclically substituted sulphones such as, for example, the compound 2-methylsulphonyl-5-(3-nitrophenyl)-1,3,4-oxadiazole, or the compound 2-(2-chlorophenyl)-5-methylsulphonyl-1,3,4-oxadiazole, have a certain fungistatic action against *Aspergillus niger* and *flavus* when used in in-vitro experiments (compare, for example, Agric. Biol. Chem. 40, 17-21 [1976] or CA 84: 121736n).

It has now been found that heterocyclically substituted sulphones of the general formula (I)

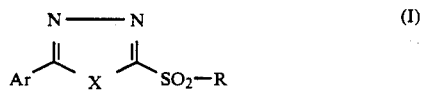

in which

Ar represents phenyl which is monosubstituted to trisubstituted by identical or different substituents, suitable substituents being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, or phenyl which is optionally monosubstituted to pentasubstituted by identical or different substituents from the series comprising halogen and/or straight-chain or branched alkyl having 1 to 4 carbon atoms, R represents straight-chain or branched alkyl having 1 to 4 carbon atoms, and X represents oxygen or sulphur, with the exception of the compounds 5-(2-chlorophenyl)- and 5-(3-nitrophenyl)-2-methylsulphonyl-1,3,4-oxadiazole, have a particularly good action against agriculturally relevant phytopathogenic fungal species, Surprisingly, the heterocyclically substituted sulphones which can be used according to the invention, of the general formula (I), show a considerably more powerful fungicidal activity towards phytopathogenic fungi in agriculture than the heterocyclically substituted sulphones which are known from the prior art.

Formula (I) provides a general definition of the heterocyclically substituted sulphones which can be used according to the invention. Compounds of the formula (I) which can preferably be used are those in which Ar represents phenyl which is monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, difluoromethyl, trifluoromethyl, trifluoromethoxy, trifluoromethylthio, methoxycarbonyl, ethoxycarbonyl, methoximinomethyl, ethoximinomethyl, methoximinoethyl, ethoximinoethyl, or phenyl which is optionally monosubstituted to trisubstituted by identical or different substituents from the series comprising fluorine, chlorine, bromine, methyl and/or ethyl, R represents methyl or ethyl and X represents oxygen, or Ar represents phenyl which is monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, difluoromethyl, trifluoromethyl, trifluoromethoxy, trifluoromethylthio, methoxycarbonyl, ethoxycarbonyl, methoximinomethyl, ethoximinomethyl, methoximinoethyl, ethoximinoethyl, or phenyl which is optionally monosubstituted to trisubstituted by identical or different substituents from the series comprising fluorine, chlorine, bromine, methyl and/or ethyl, R represents methyl or ethyl and X represents sulphur, with the exception of 5-(2-chlorophenyl)- and 5-(3-nitrophenyl)-2-methylsulphonyl-1,3,4-oxadiazole.

Compounds of the formula (I) which must be emphasised very particularly are those in which Ar represents 4-chlorophenyl or 4-methylphenyl, R represents methyl and X represents oxygen, or Ar represents 4-chlorophenyl, R represents methyl and X represents sulphur.

The following heterocyclically substituted sulphones of the general formula (I) may be mentioned individually in addition to the compounds mentioned in the Preparation Examples:

| Ar | R | X | Ar | R | X |
|---|---|---|---|---|---|
| Br-phenyl | CH₃ | O/S | F,F-phenyl | CH₃ | O/S |
| Br-phenyl | CH₃ | O/S | Cl,F-phenyl | CH₃ | O/S |
| Br-phenyl | CH₃ | O/S | F,Cl-phenyl | CH₃ | O/S |

-continued $$\underset{Ar}{\overset{N=N}{\underset{\|}{\text{C}}}}\underset{X}{\overset{}{\underset{}{\text{C}}}}\underset{SO_2-R}{\overset{}{}}\qquad(I)$$

| Ar | R | X | Ar | R | X |
|---|---|---|---|---|---|
| 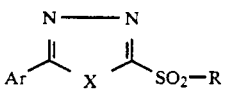 | CH$_3$ | O/S | 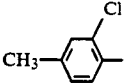 | CH$_3$ | O/S |
| 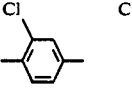 | CH$_3$ | O/S | 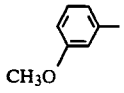 | CH$_3$ | O/S |
| 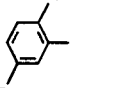 | CH$_3$ | O/S | 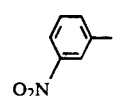 | CH$_3$ | O/S |
| 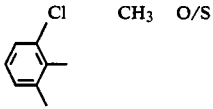 | CH$_3$ | O/S | 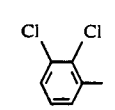 | CH$_3$ | O/S |
| 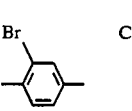 | CH$_3$ | O/S | 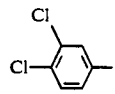 | CH$_3$ | O/S |
| 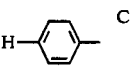 | CH$_3$ | O/S | 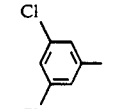 | CH$_3$ | O/S |
| 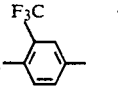 | CH$_3$ | O/S | 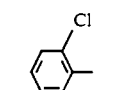 | CH$_3$ | O/S |
| 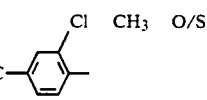 | CH$_3$ | O/S | 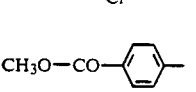 | CH$_3$ | O/S |
| 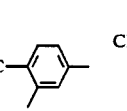 | CH$_3$ | O/S |  | CH$_3$ | O/S |
| 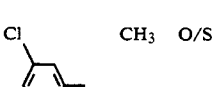 | CH$_3$ | O/S | 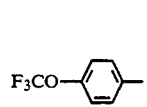 | CH$_3$ | O/S |
| 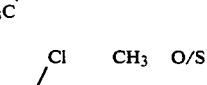 | CH$_3$ | O/S |  | CH$_3$ | O/S |
| 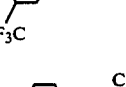 | CH$_3$ | O/S |  | CH$_3$ | O/S |

The heterocyclically substituted sulphones of the formula (I) which can be used according to the invention are known (compare, for example, J. Chem. Soc., Perkin Trans. 1, 1983, 967-971; J. Am. Chem. Soc. 105, 902-906 [1983]; JP 52010421/1977; Farmaco, Ed. Sci., 32, 414-429 [1977] or CA 87: 95447j; Agric. Biol. Chem. 40, 17-21 [1976] or CA 84: 121736n; Indian J. Chem., 7, 760-765 [1969]; Bull. Chim. Farm. 106, 826-836 [1967] or CA 69: 27340x) or can be obtained with the aid of generally customary, known processes (compare, for example, J. Amer. Chem. Soc. 105, 902 [1983]; J. Amer. Chem. Soc. 77, 400 [1955] and the Preparation Examples).

The active compounds which can be used according to the invention have a powerful action against phytopathogenic fungi and can be employed in agricultural practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum;*

Cercospora species, such as, for example, *Cercospora canescens;*

Alternaria species, such as, for example, *Alternaria brasicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the compounds which can be used according to the invention can be employed with particularly good success for combating cereal diseases, such as, for example, against the pathogen causing powdery mildew of cereals (*Erysiphe graminis*) or against the pathogen causing glume blotch on wheat (*Septoria nodorum*) or against the pathogen causing net blotch disease of barley (*Pyrenophora teres*), against Fusarium species on cereals, or for combating diseases in rice growing, such as, for example, against the pathogen causing rice blast disease (*Pyricularia oryzae*), or for combating diseases in fruit and vegetable growing, such as, for example, against the pathogen causing apple scab (*Venturia inaequalis*). In this context, the active compounds which can be used according to the invention also show curative and systemic activity, besides protective properties.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds such as fungicides, insecticides, acaricides and herbicides, and in mixtures with fertilizers and growth regulators.

The active compounds can be employed as such, in the form of their formulations or in the use forms, prepared from these formulations, such as ready-for-use solutions, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultra-low-volume process, or to inject the preparation of active compound, or the active compound itself, into the soil. The seed of the plants can also be treated.

In the treatment of parts of plants, the active compound concentrations in the use forms can be varied within a substantial range. They are generally between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of the soil, active compound concentrations of 0.00001 to 0.1% by weight, preferably 0.0001 to 0.02%, are necessary at the site of action.

PREPARATION EXAMPLES

EXAMPLE 1

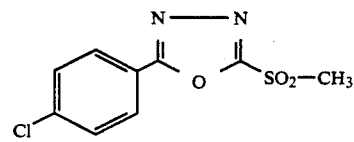

A solution of 180.9 g (1.145 mol) of potassium permanganate in 3600 ml of water is added dropwise with stirring at room temperature to 123.5 g (0.546 mol) of 5-(4-chlorophenyl)-2-methylthio-1,3,4-oxadiazole in 1000 ml of glacial acetic acid. 40 percent strength aqueous sodium hydrogen sulphite solution is subsequently added until the mixture is decolourised, and precipitated reaction product is filtered off and recrystallised from ethanol.

92.5 g (66% of theory) of 5-(4-chlorophenyl)-2-methylsulphonyl-1,3,4-oxadiazole of melting point 159° C. to 160° C. are obtained.

Preparation of the starting compound

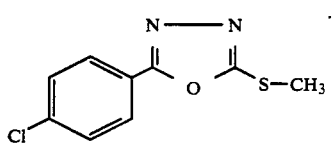

12 g (0.21 mol) of potassium hydroxide, dissolved in 18 ml of water, are added to a suspension of 34.1 g (0.2 mol) of p-chlorobenzoyl hydrazide in 300 ml of ethanol, and 16.5 g (0.22 mol) of carbon disulphide are subsequently slowly added dropwise at room temperature, with stirring. When the addition has ended, the mixture is diluted with 200 ml of ethanol and refluxed for 16 hours, 30.8 g (0.22 mol) of methyl iodide are then added dropwise with stirring, the mixture is subsequently cooled to 0° C. and stirred for 30 minutes at this temperature, and precipitated reaction product is filtered off with suction and recrystallised from ethanol.

38 g (84% of theory) of 5-(4-chlorophenyl)-2-methylthio-1,3,4-oxadiazole of melting point 121° C. to 123° C. are obtained.

The following heterocyclically substituted sulphones of the general formula (I)

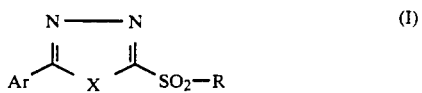

are obtained in a corresponding fashion.

| Ex. No. | Ar | R | X | Melting point °C. |
|---|---|---|---|---|
| 2 | 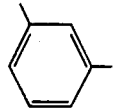 | CH₃ | S | 190–192 |
| 3 | 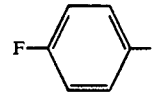 | CH₃ | O | 128–130 |
| 4 | 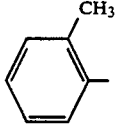 | CH₃ | O | 105 |
| 5 | 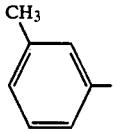 | CH₃ | O | 140 |
| 6 | 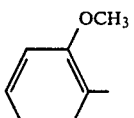 | CH₃ | O | 123 |
| 7 | 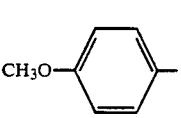 | CH₃ | O | 111–113 |
| 8 | 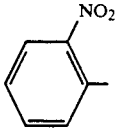 | CH₃ | O | 103 |
| 9 | 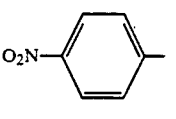 | CH₃ | O | 146–148 |
| 10 | 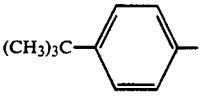 | CH₃ | O | 154–156 |
| 11 | 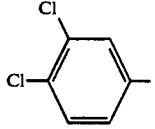 | CH₃ | O | 108–110 |
| 12 | 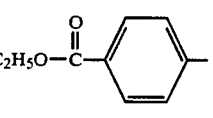 | CH₃ | O | 168–172 |
| 13 | 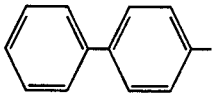 | CH₃ | O | 94–96 |
| 14 | Cl–⟨ ⟩– (3,4-diCl) | CH₃ | O | 166–168 |
| 15 | C₂H₅O–C(O)–⟨ ⟩– | CH₃ | O | oil |
| 16 | ⟨ ⟩–⟨ ⟩– (biphenyl) | CH₃ | O | 170–173 |

-continued

| Ex. No. | Ar | R | X | Melting point °C. |
|---|---|---|---|---|
| 17 | 3-CF₃-C₆H₄- | CH₃ | O | 90-94 |
| 18 | 4-CH₃-C₆H₄- | CH₃ | O | oil |
| 19 | 3-F-C₆H₄- | CH₃ | S | 91 |
| 20 | 3-CH₃-4-F-C₆H₃- | CH₃ | S | 112 |
| 21 | 3,5-Cl₂-C₆H₃- | CH₃ | S | 138 |
| 22 | 2,5-F₂-C₆H₃- | CH₃ | S | 124 |
| 23 | 3,5-F₂-C₆H₃- | CH₃ | S | 125 |
| 24 | 4-(CH₃)₂N-C₆H₄- | CH₃ | S | |
| 25 | 3,4-Cl₂-C₆H₃- | CH₃ | S | 181 |
| 26 | 3-F-4-Cl-C₆H₃- | CH₃ | S | 91 |
| 27 | 3-CH₃-4-F-C₆H₃- | CH₃ | S | 84 |
| 28 | 3-Cl-5-F-C₆H₃- | CH₃ | S | 107 |
| 29 | 3-CH₃-4-OCF₃-C₆H₃- | CH₃ | S | 58 |
| 30 | 3,5-(CH₃,CF₃)-C₆H₃- | CH₃ | S | 82 |

Use Example

In the Use Examples which follow, the compounds listed below were employed as comparison substances:

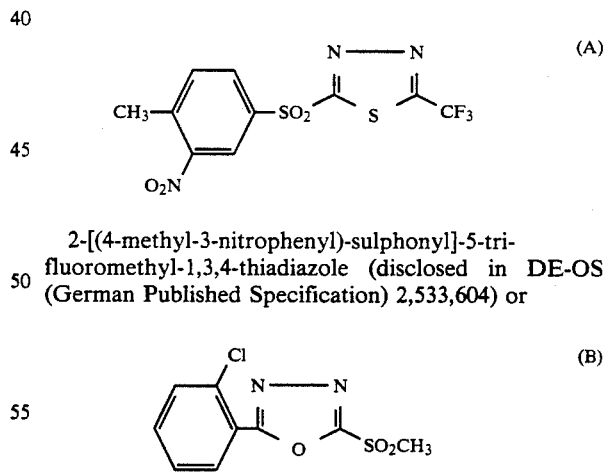

(A)

2-[(4-methyl-3-nitrophenyl)-sulphonyl]-5-trifluoromethyl-1,3,4-thiadiazole (disclosed in DE-OS (German Published Specification) 2,533,604) or

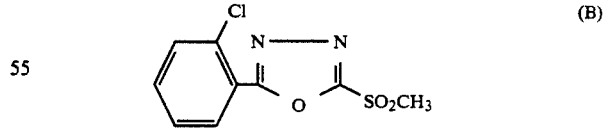

(B)

5-(2-chlorophenyl)-2-methylsulphonyl-1,3,4-oxadiazole (known from Agr. Biol. Chem. 40 (1), pp. 17–21 (1976)).

Example A

Botrytis test (dwarf beans)/protective
Solvent: 4.7 parts by weight of acetone
Emulsifier: 0.3 parts by weight of alkyl-aryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small agar pieces, covered with growth of *Botrytis cinerea*, are placed on each leaf. The inoculated plants are placed in a darkened, humid chamber at 20° C. 3 days after inoculation, the size of the lesions on the leaves is evaluated.

In this test, a clearly superior activity compared with the prior art is shown, for example, by the compounds of the following Preparation Examples:

TABLE A

Botrytis test (beans)/protective

| Active compound | Degree of effectiveness in % of the untreated control at an active compound concentration of 100 ppm |
|---|---|
| Known: | |
| 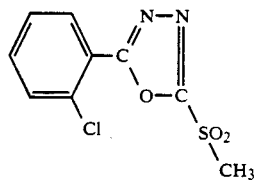 | 0 |
| According to the invention: | |
| 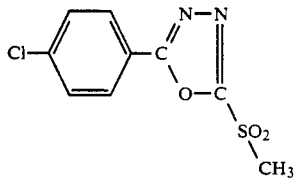 | 100 |
| 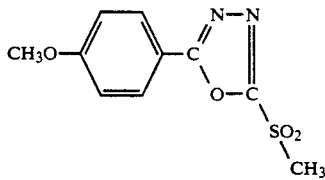 | 52 |
| 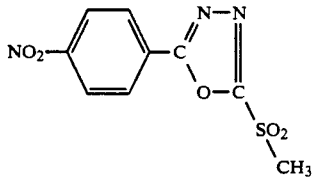 | 60 |
| 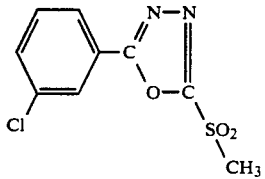 | 99 |

TABLE A-continued

Botrytis test (beans)/protective

| Active compound | Degree of effectiveness in % of the untreated control at an active compound concentration of 100 ppm |
|---|---|
| 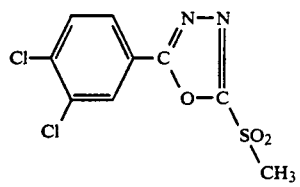 | 100 |
| 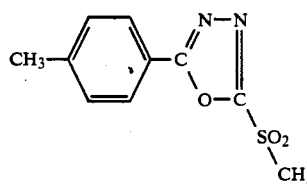 | 55 |
| 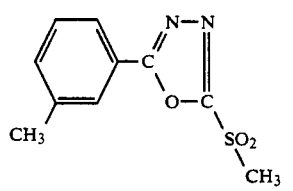 | 74 |

Example B

Venturia test (apple)/protective

Solvent: 4.7 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compound according to Preparation Example 1.

TABLE B

Venturia test (apple)/protective

| Active compound | Degree of effectiveness in % of the untreated control at an active compound concentration of 5 ppm |
|---|---|
| <br>(A) (known) | 73 |
| 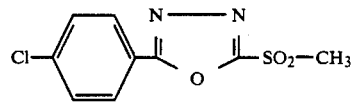<br>(1) | 93 |

We claim:

1. A method of combating phytopathogenic fungi in agriculture which comprising applying to such fungi or to a locus from which it is desired to exclude such fungi a fungicidal by effective amount of a substituted sulphone of the formula (I)

$$\underset{Ar}{\overset{N\text{---}N}{\underset{X}{\parallel}\phantom{xx}\underset{SO_2\text{---}R}{\parallel}}}$$ (I)

in which

Ar represents monosubstituted to trisubstituted phenyl by identical or different substituents selected from the group consisting of halogen, cyano, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, unsubstituted phenyl and monosubstituted to pentasubstituted phenyl by identical or different substituents selected from the group consisting of halogen and straight-chain or branched alkyl having 1 to 4 carbon atoms, R represents straight-chain or branched alkyl having 1 to 4 carbon atoms, and X represents oxygen with the exception of the compound 5-(2-chlorophenyl)-2-methylsulphonyl-1,3,4-oxadiazole.

2. The method according to claim 1, in which

Ar represents phenyl which is monosubstituted to trisubstituted by identical or different substituents selected from the group consisting of fluorine, chlorine, bromine, cyano, methyl, ethyl, n- or i-propyl, n-, i-, s- or t-butyl, methoxy, ethoxy, n- or i-propoxy, methylthio, difluoromethyl, trifluoromethyl, trifluoromethoxy, trifluoromethylthio, methoxycarbonyl, ethoxycarbonyl, methoximinomethyl, ethoximinomethyl, methoximinoethyl, ethoximinoethyl, unsubstituted phenyl and monosubstituted to trisubstituted phenyl, by identical or different substituents selected from the group consisting of fluorine, chlorine, bromine, methyl and ethyl, R represents methyl or ethyl and X represents oxygen, with the exception of 5-(2-chlorophenyl)-2-methylsulphonyl-1,3,4-oxadiazole.

3. The method according to claim 1, wherein such compound is 5-(4-chlorophenyl)-2-methylsulphonyl-1,3,4-oxadiazole of the formula

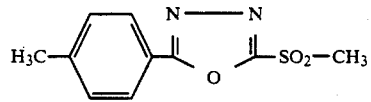

4. The method according to claim 1, wherein such compound is 5-(4-methylphenyl)-2-methylsulphonyl-1,3,4-oxadiazole of the formula H₃C—⟨phenyl⟩—(oxadiazole)—SO₂—CH₃

* * * * *

UNITED STATES PATENT AND TRADEMARK OFFICE
CERTIFICATE OF CORRECTION

PATENT NO. : 5,166,165
DATED : November 24, 1992
INVENTOR(S) : Kleefeld et al.

It is certified that error appears in the above-identified patent and that said Letters Patent is hereby corrected as shown below:

| | |
|---|---|
| Col. 13, claim 1 line 4 | Delete " fungicidal by " and substitute -- fungicidally -- |
| Col. 14, line 7 | After " oxygen " insert -- , -- |
| Col. 14, line 21 | After " phenyl " (2nd occurrence) delete " , " |

Signed and Sealed this

Third Day of May, 1994

Attest:

BRUCE LEHMAN

Attesting Officer

Commissioner of Patents and Trademarks